United States Patent [19]
Smith et al.

[11] Patent Number: 5,807,338
[45] Date of Patent: Sep. 15, 1998

[54] MODULAR TROCAR SYSTEM AND METHODS OF ASSEMBLY

[75] Inventors: Robert C. Smith, Danbury; Martin J. Nohilly, Trumbull; Marc J. Theroux, Bethel; Richard D. Gresham, Monroe; Timothy O. VanLeeuwen, Brookfield, all of Conn.

[73] Assignee: United States Surgical Corporation, Norwalk, Conn.

[21] Appl. No.: 546,009

[22] Filed: Oct. 20, 1995

[51] Int. Cl.⁶ .................................................. A61M 5/178
[52] U.S. Cl. .................... 604/164; 604/234; 606/167; 606/170; 606/184
[58] Field of Search ..................... 604/164, 165, 604/152, 192, 158, 49, 264; 606/167, 170, 184

[56] References Cited

U.S. PATENT DOCUMENTS

| | | |
|---|---|---|
| 1,531,213 | 3/1925 | Nimmer . |
| 1,742,497 | 1/1930 | Dickinson . |
| 2,389,355 | 11/1945 | Goland et al. . |
| 3,539,034 | 11/1970 | Tafeen . |
| 3,713,447 | 1/1973 | Adair . |
| 3,994,287 | 11/1976 | Turp et al. . |
| 4,436,519 | 3/1984 | O'Neill . |
| 4,517,962 | 5/1985 | Heckele . |
| 4,535,773 | 8/1985 | Yoon . |
| 4,569,131 | 2/1986 | Falk et al. . |
| 4,601,710 | 7/1986 | Moll ........................................ 604/165 |
| 4,609,370 | 9/1986 | Morrison . |
| 4,626,245 | 12/1986 | Weinstein . |
| 4,649,904 | 3/1987 | Krauter et al. . |
| 4,654,030 | 3/1987 | Moll et al. . |
| 4,655,752 | 4/1987 | Honkanen et al. . |
| 4,769,018 | 9/1988 | Wilson . |
| 4,772,265 | 9/1988 | Walter . |
| 4,798,591 | 1/1989 | Okada . |
| 4,902,280 | 2/1990 | Lander .................................... 604/165 |

(List continued on next page.)

FOREIGN PATENT DOCUMENTS

| | | |
|---|---|---|
| 0604197 | 6/1994 | European Pat. Off. . |
| 1064445 | 5/1954 | France . |
| 378629 | 7/1923 | Germany . |
| 4238596 | 6/1994 | Germany . |
| 1430092 | 3/1976 | United Kingdom . |
| WO 93/04717 | 3/1993 | WIPO . |
| WO9315675 | 8/1993 | WIPO . |
| WO9404082 | 3/1994 | WIPO . |
| WO 94/13335 | 6/1994 | WIPO . |
| WO 95/07663 | 3/1995 | WIPO . |

OTHER PUBLICATIONS

Karl Storz, Endosckope "Spare Parts Accessories", (catalog, 54 pages—pp. 12 & 30 missing), approx. Apr. 1989.

*Primary Examiner*—Corrine M. McDermott
*Assistant Examiner*—Cris L. Rodriguez

[57] ABSTRACT

A modular trocar system is provided which includes an obturator assembly, and a cannula assembly defining a longitudinal passageway therethrough configured and dimensioned to slidably receive the obturator assembly, the cannula assembly including a housing which includes a valve assembly and a first mating portion, and a cannula defining a passageway of a predetermined dimension therethrough, the cannula including a second mating portion disposed thereon, the cannula and housing movable alternately between a spaced apart relative orientation and an attached orientation wherein the first and second mating portions are engaged. A method of assembly is also provided and includes the steps of connecting a shield member of a first predetermined configuration and dimension to a first housing section, attaching a knife blade assembly of a second predetermined configuration and dimension to the first housing section with a single motion wherein the attachment permits rotation of the knife blade relative to the first housing section, and attaching the first housing section to a second housing section with a quick connect mechanism which includes first and second mating portions such that the first and second housing sections are movable from a spaced apart position to a connected position in a single motion.

4 Claims, 9 Drawing Sheets

U.S. PATENT DOCUMENTS

| | | | |
|---|---|---|---|
| 4,922,602 | 5/1990 | Mehl . | |
| 4,924,851 | 5/1990 | Ognier et al. . | |
| 4,931,042 | 6/1990 | Holmes et al. | 604/164 |
| 4,946,133 | 8/1990 | Johnson et al. . | |
| 4,973,321 | 11/1990 | Michelson . | |
| 4,997,419 | 3/1991 | Lakatos et al. . | |
| 5,009,643 | 4/1991 | Reich et al. . | |
| 5,013,300 | 5/1991 | Williams . | |
| 5,030,206 | 7/1991 | Lander . | |
| 5,057,082 | 10/1991 | Burchette, Jr. | 604/164 |
| 5,066,288 | 11/1991 | Deneiga et al. . | |
| 5,104,382 | 4/1992 | Brinkeroff et al. . | |
| 5,112,321 | 5/1992 | Hiltebrandt . | |
| 5,116,353 | 5/1992 | Green . | |
| 5,122,122 | 6/1992 | Allgood . | |
| 5,129,884 | 7/1992 | Dysarz . | |
| 5,147,314 | 9/1992 | Vaillancourt . | |
| 5,152,754 | 10/1992 | Plyley et al. . | |
| 5,158,552 | 10/1992 | Borgia et al. . | |
| 5,176,648 | 1/1993 | Holmes et al. . | |
| 5,176,651 | 1/1993 | Allgood et al. . | |
| 5,201,714 | 4/1993 | Gentelia et al. . | |
| 5,209,736 | 5/1993 | Stephens et al. . | |
| 5,211,633 | 5/1993 | Stouder, Jr. . | |
| 5,224,930 | 7/1993 | Spaeth et al. . | |
| 5,226,426 | 7/1993 | Yoon . | |
| 5,242,412 | 9/1993 | Blake, III . | |
| 5,261,888 | 11/1993 | Semm . | |
| 5,275,583 | 1/1994 | Crainicm | 604/165 |
| 5,295,993 | 3/1994 | Green | 604/164 |
| 5,300,035 | 4/1994 | Clement . | |
| 5,308,576 | 5/1994 | Green et al. . | |
| 5,312,354 | 5/1994 | Allen et al. | 604/164 |
| 5,322,503 | 6/1994 | Desai . | |
| 5,324,270 | 6/1994 | Kayan et al. . | |
| 5,356,394 | 10/1994 | Farley et al. . | |
| 5,380,288 | 1/1995 | Hart et al. . | |
| 5,383,860 | 1/1995 | Lau . | |
| 5,395,342 | 3/1995 | Yoon . | |
| 5,445,630 | 8/1995 | Richmond . | |
| 5,456,673 | 10/1995 | Ziegler et al. . | |
| 5,460,615 | 10/1995 | Storz . | |
| 5,486,190 | 1/1996 | Green | 604/164 |
| 5,496,270 | 3/1996 | Nettekoven . | |
| 5,496,280 | 3/1996 | Vandenbroek et al. . | |
| 5,496,289 | 3/1996 | Wenstrom, Jr. . | |

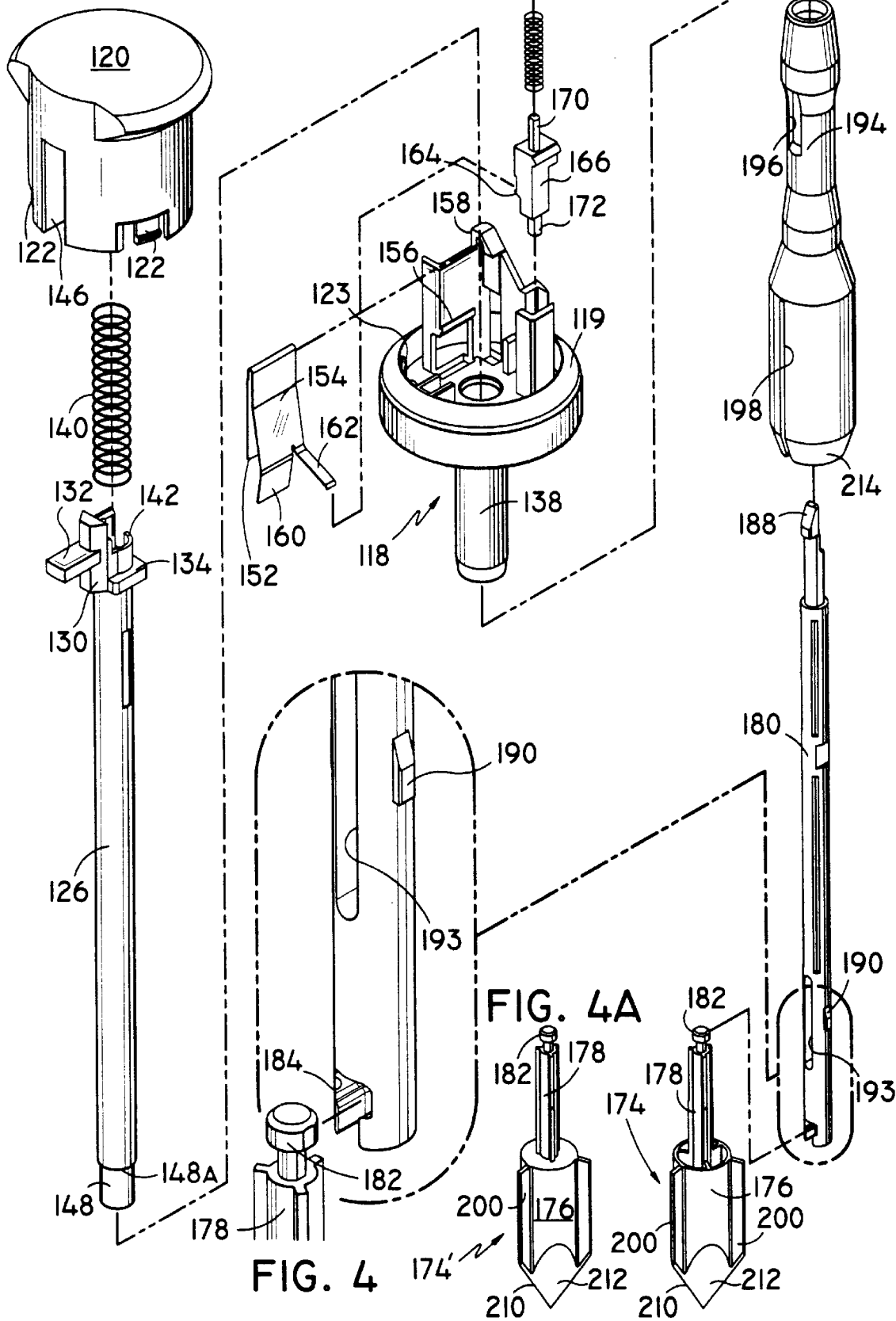

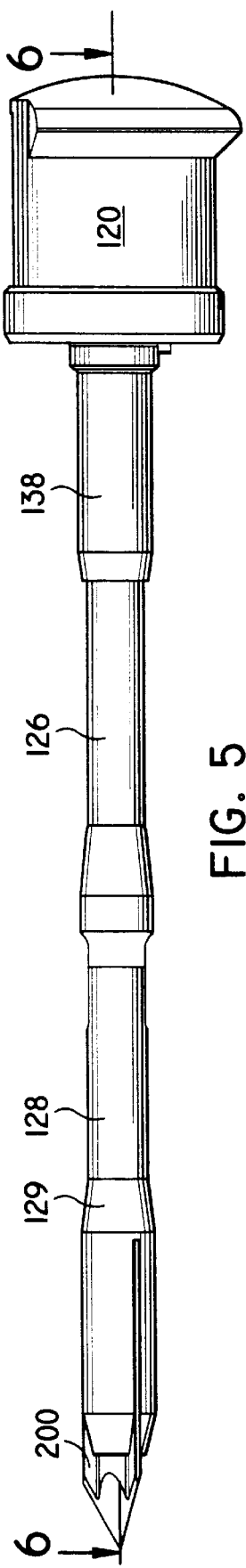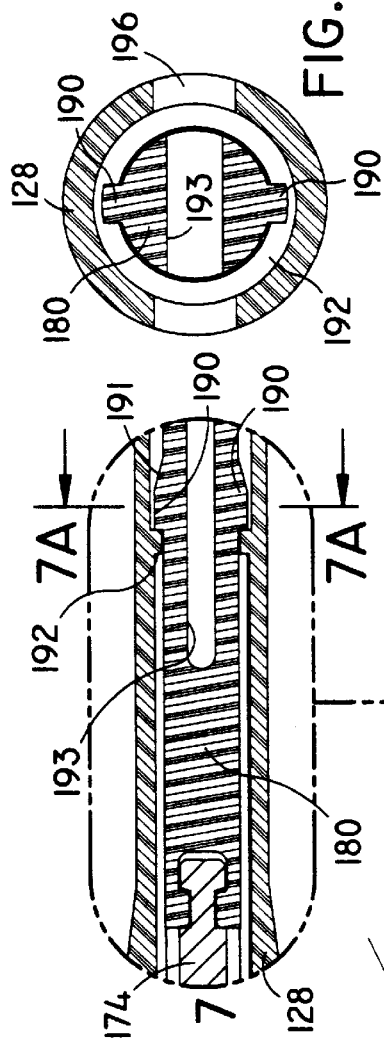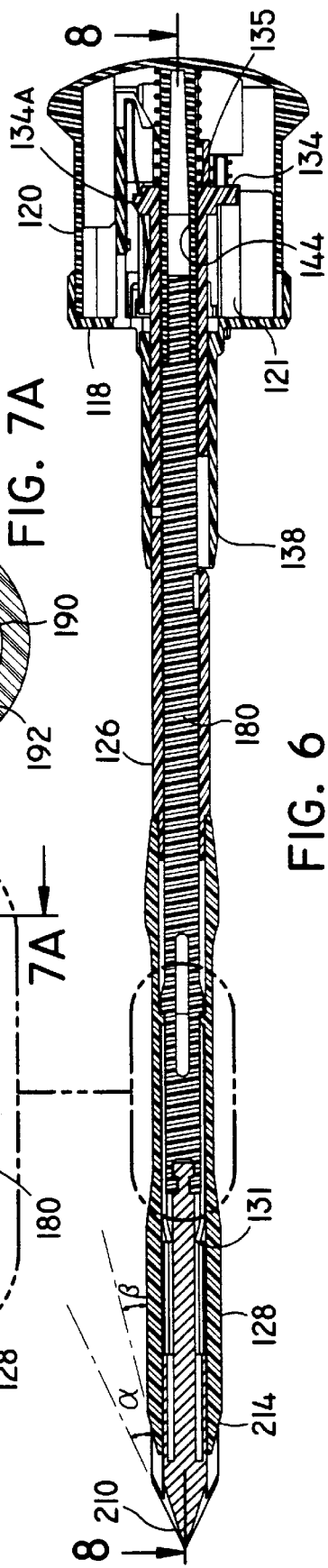

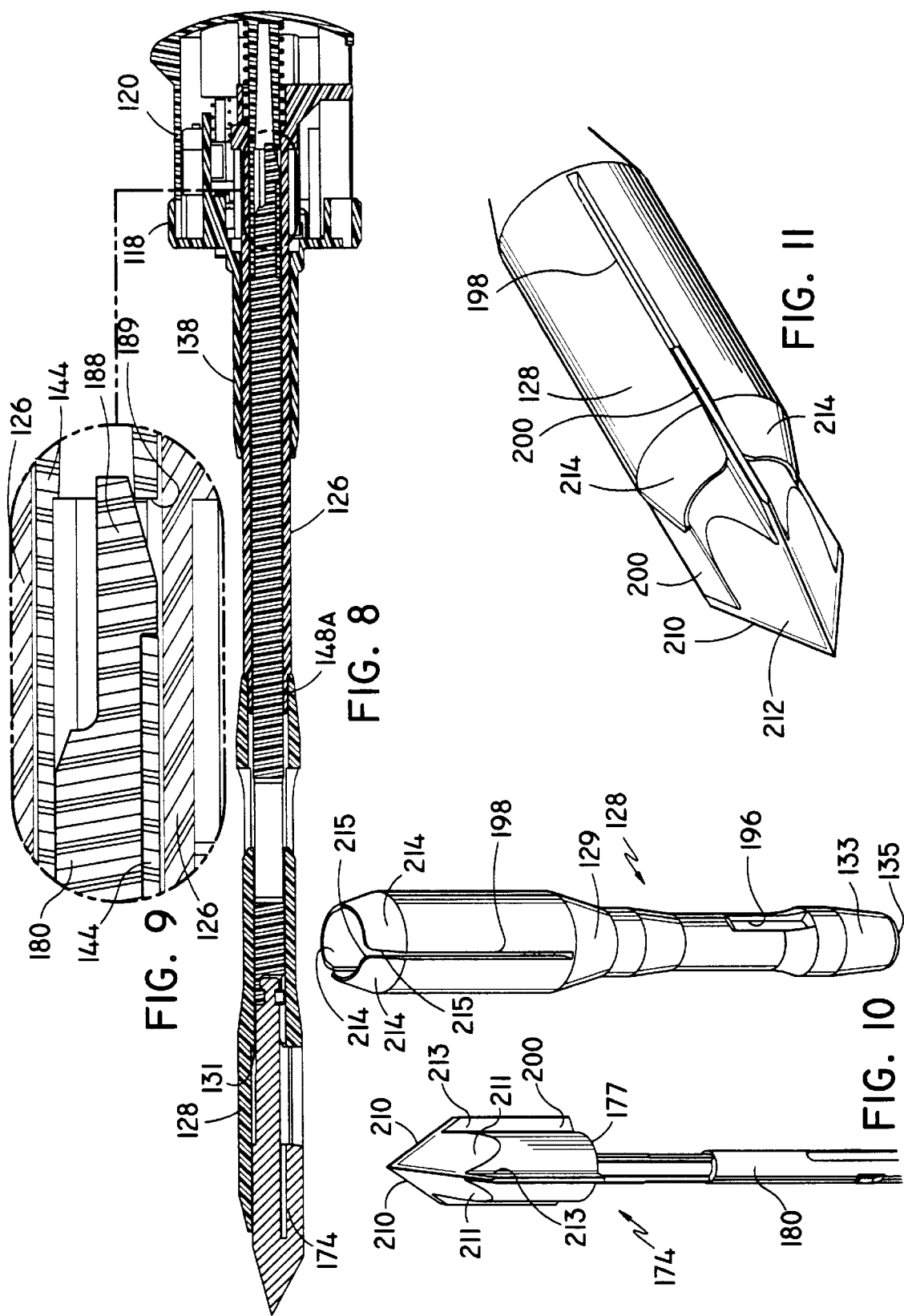

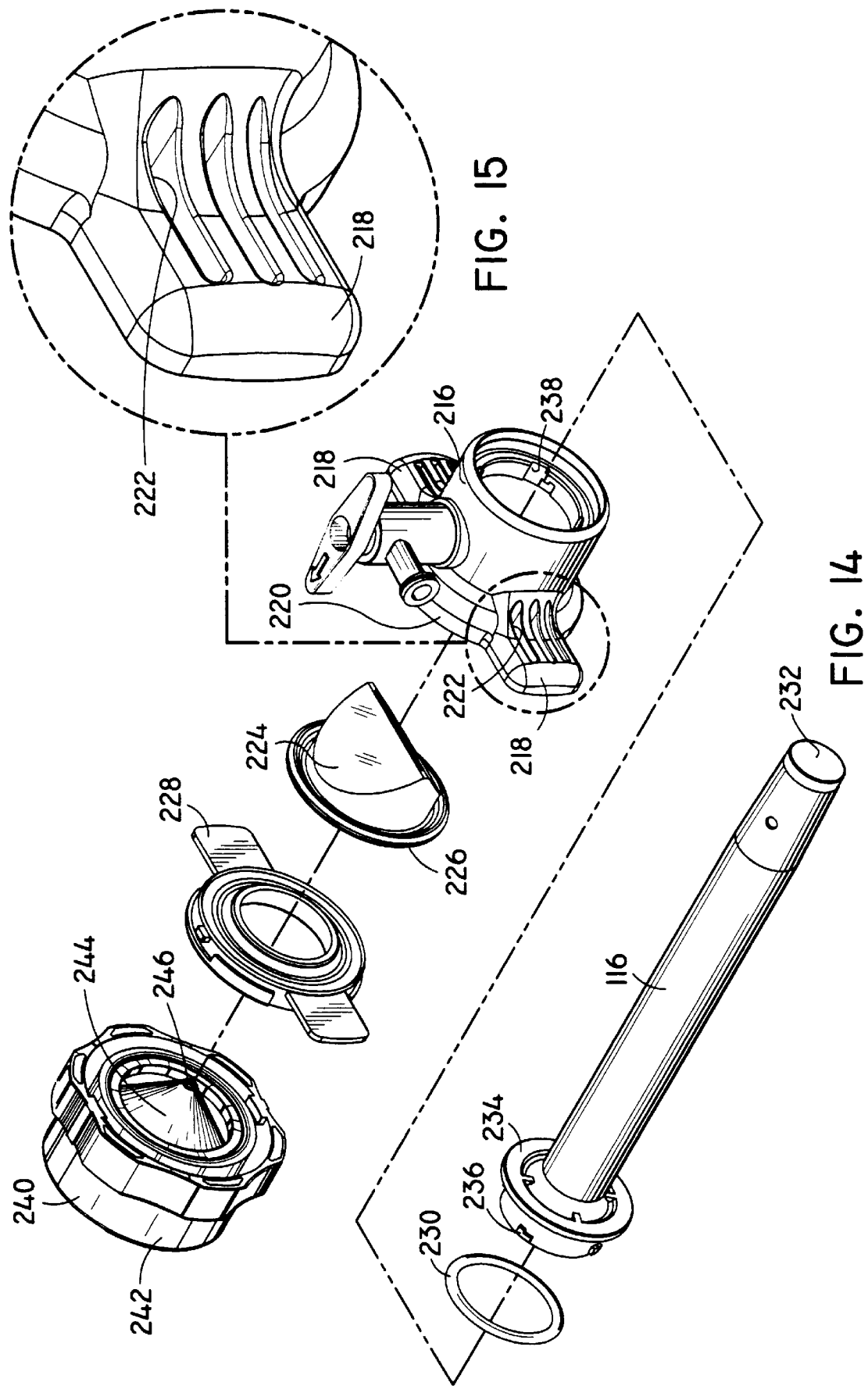

MODULAR TROCAR SYSTEM AND METHODS OF ASSEMBLY

BACKGROUND

1. Technical Field

The present disclosure relates to trocar systems for inserting cannulas into patients, and more particularly to modular trocar systems and methods of assembly of trocar systems.

2. Background of Related Art

Minimally invasive surgical procedures where trocar systems are desirable or even necessary are continually increasing in number and variety. These procedures call upon surgeons to utilize an array of variously sized surgical equipment, e.g., graspers, dissectors, clip appliers, staplers, retractors, imaging systems, and the like. Accordingly, trocar assemblies having variously sized obturators and cannulas are required, e.g. 3–15 mm, to facilitate the range of minimally invasive procedures while minimizing the size of each trocar entry to the extent possible.

Presently, placement of each different diameter cannula requires the use of a specially sized obturator assembly. In other words, to introduce a 5 mm cannula, a 5 mm obturator is required; to introduce a 10 mm cannula, a 10 mm obturator is required; and so on. Manufacturers of trocar assemblies must therefore produce and inventory numerous different sized housings and operative components to allow the manufacture of each particular obturator and cannula variation to be marketed. For obvious commercial reasons, health care providers and medical equipment distributors of trocar assemblies must maintain appropriate inventories of each product variation to meet customer demand as it arises.

WO 95/07663 to Vidal et al. discloses one approach to addressing the variety of customer needs in the field of trocar assemblies. Vidal et al. disclose a plurality of obturator tips that are adapted to be removably received by an obturator shaft, e.g., through a detent/leaf spring arrangement or a lug/groove arrangement. While a variety of cutting blade geometries are proposed from which the surgeon may select, each of the disclosed obturator tips is the same diameter so that the completed obturator assembly may be utilized with a cannula of preselected diameter.

It is also known to provide operative surgical instruments with interchangeable working ends. For example, WO 94/13335 to Dorsey discloses a "quick disconnect" arrangement for a suction/irrigation system that allows interchange between a variety of probes of differing shapes and orientation. See also U.S. Pat. No. 5,322,503 to Desai which discloses an instrument that is adapted to receive a variety of electrostatic probes.

A further factor of significance in the design and use of trocar systems is the ease with which the trocar system passes through the body wall so as to position the cannula thereacross. Thus, efforts have been expended to minimize the penetration force of the trocar system while maintaining maximum surgeon control and safety. U.S. Pat. No. 4,601,710 to Moll discloses several trocar designs which include a spring biased safety shield adapted to cover the cutting blade upon entry into the body cavity. In one embodiment (see FIGS. 1–5B), the safety shield is slotted and the blade is configured to extend through the slots, thereby increasing the effective diameter of the blade incision. See also U.S. Pat. No. 5,066,288 to Deneiga et al.

Despite these earlier efforts in the fields of interchangeability, a need exists for a trocar system that is truly modular. That is, a trocar system wherein various is components thereof may be readily interchangeable and certain components standardized to facilitate manufacture and use across a broader spectrum of product lines.

Moreover, improvements in trocar design which might minimize penetration force while maintaining surgeon control and safety during trocar penetration are always warranted and to be welcomed.

SUMMARY

The present disclosure provides a modular trocar system which addresses limitations associated with conventional manufacture and assembly of trocar systems. The presently disclosed modular trocar system satisfies the need for greater inventory flexibility and management as well as achieving greater manufacturing efficiencies. In particular, the presently disclosed modular trocar system permits utilization of some of the same components across many different sized trocar products. The present disclosure also provides a modular trocar system which minimizes penetration force while maintaining surgeon control and providing an enhanced margin of safety during trocar entry.

One particular embodiment of the present disclosure provides a modular trocar system which includes (i) an obturator assembly that includes an obturator, a knife and a safety shield movable with respect to the obturator and knife, and (ii) a cannula assembly defining a longitudinal passageway therethrough configured and dimensioned to slidably receive at least a portion of the obturator assembly. The cannula assembly includes a housing which includes a valve assembly and a first mating portion, and a cannula defining a passageway of a predetermined dimension therethrough, the cannula including a second mating portion disposed thereon, the cannula and housing being movable between a spaced apart relative orientation and an attached orientation wherein the first and second mating portions are engaged.

Preferably, a seal member is disposed between the housing and the cannula to provide a fluid-tight seal between the two elements.

In an alternative embodiment, a modular trocar system is provided which includes an obturator assembly that includes an obturator, a knife and a shield movable with respect to the obturator and knife, as well as a housing having a first mating portion formed thereon. The safety shield is defined by a shield member of a first predetermined configuration and dimension movably mounted with respect to the housing, and a knife blade assembly of a predetermined configuration and dimension and having a second mating portion formed thereon. The knife blade assembly is adapted to cooperate with the safety shield and preferably includes a knife and a distal shield member movably mounted with respect to the knife. The knife blade assembly is adapted to be attached to the housing with a single motion.

A cannula assembly is also preferably provided which defines a longitudinal passageway therethrough configured and dimensioned to slidably receive at least a portion of the obturator assembly, the cannula assembly including a housing having a valve assembly disposed thereon and a cannula extending from the housing.

The knife assembly preferably includes a knife rotatably connected to a rod with the second mating portion being formed on the rod. The knife preferably has a circular base portion and a sharpened tip formed at a distal end of the base portion. Additionally, the knife may preferably include a plurality of cutting edges which extend at least partially outwardly from the circular base portion. The sharpened tip is formed by the intersection of the plurality of cutting edges such that a planar surface is formed and extends between each adjacent pair of cutting edges over at least a portion of the length of the respective cutting edges.

The knife assembly also preferably includes a distal shield member that is movably mounted with respect to the knife. The distal shield member preferably includes a plurality of slots positioned to receive corresponding cutting edges therewithin, and a plurality of inwardly tapered, substantially conical faces defined between adjacent slots which are adapted to interact with the corresponding planar surfaces defined on the knife so as to minimize penetration force.

The present disclosure also provides a cannula assembly for use with a trocar system, the cannula assembly including (i) a housing which includes a valve assembly and a first mating portion and (ii) a cannula defining a passageway of a predetermined configuration and dimension therethrough, the cannula including a second mating portion disposed thereon.

The cannula is preferably molded, having a substantially constant inner diameter and an outer diameter that is gradually reduced in the distal direction over its distal-most portion. For example, a preferred cannula includes a slightly larger inner diameter at its proximal end to accommodate the introduction of instruments therein, e.g., of about 2–3 cms length, and a gradually reduced outer diameter over the final portion, e.g., about the distal-most 2–3 cms, to minimize penetration force. The remainder of the outer diameter of the cannula is preferably constant, thereby minimizing the likelihood that the cannula will pull out from the incision. The cannula and housing are preferably movable between a spaced apart relative orientation to an attached orientation wherein the first and second mating portions are engaged.

An obturator assembly is also provided in the present disclosure. Included in the obturator assembly are a housing including a first mating portion, a shield member of a first predetermined configuration and dimension movably mounted with respect to the housing, a knife blade assembly of a predetermined configuration and dimension and having a second mating portion formed thereon and adapted to engage the first mating portion such that the knife blade assembly is attached to the housing with a single motion. The knife blade assembly preferably includes a knife and a distal shield member which is movably mounted with respect to the knife, the distal shield member assuming an abutting relation with the shield member when the knife blade is assembly is attached to the housing.

A method of assembling an obturator assembly for use in a trocar system is also provided and includes the steps of (i) mounting a shield member of a first predetermined configuration and dimension to a first housing section, (ii) mounting a distal shield member with respect to a knife blade to define a knife blade assembly of a second predetermined configuration and dimension, and (iii) connecting the knife blade assembly to the first housing section with a single motion wherein the connection permits rotation of the knife blade relative to the first housing section A further method is provided for assembling a cannula assembly for use with an obturator assembly as part of a trocar system, including the steps of (i) aligning a first mating portion formed on a housing with a second mating portion formed on a cannula which defines a passageway of a predetermined size therethrough, (ii) moving the housing and the cannula from a spaced apart relative orientation to an attached orientation, wherein the first and second mating portions are engaged, and (iii) forming a fluid-tight seal between the housing and the cannula. The housing preferably includes a valve assembly disposed in a passageway formed between an open proximal end and an open distal end thereof.

BRIEF DESCRIPTION OF THE DRAWINGS

Various embodiments are described herein with reference to the drawings, wherein:

FIG. 3 is a further perspective view of the embodiment of FIG. 1 with parts separated, which shows the obturator assembly components;

FIG. 4 is an enlarged view of the indicated area of detail of FIG. 3;

FIG. 4A is perspective view of an alternative knife blade for use with the modular trocar system;

FIG. 5 is a plan view of the embodiment of FIG. 1, which shows the knife shield in the retracted position;

FIG. 6 is a cross-section view taken along section line 6—6 of FIG. 5;

FIG. 7 is an enlarged view of the indicated area of detail shown in FIG. 6;

FIG. 7A is a cross-section view taken along section line A13 A of FIG. 7;

FIG. 8 is a cross-section view taken along section lines 813 8 of FIG. 6;

FIG. 9 is an enlarged view of the area of detail indicated in FIG. 8;

FIG. 10 is a perspective view showing the distal end of the obturator assembly and the knife shield;

FIG. 11 is a perspective view of the distal end of the modular trocar system embodiment of FIG. 1 showing the knife in a fully exposed position;

FIG. 14 is a perspective view with parts separated of the cannula assembly of the embodiment of FIG. 1;

FIG. 15 is an enlarged view of the indicated area of detail of FIG. 14;

DETAILED DESCRIPTION OF PREFERRED EMBODIMENTS

Figure 1:
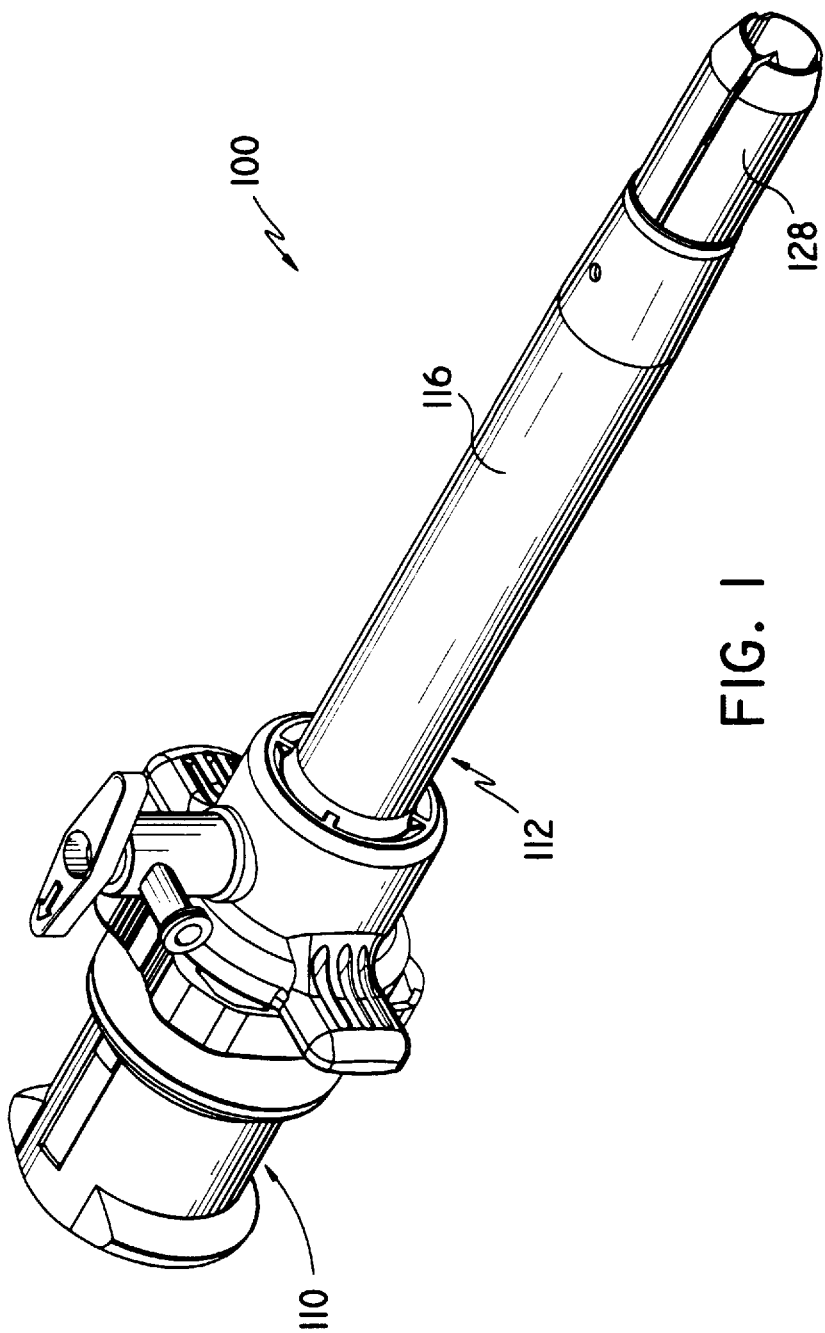
FIG. 1 is a perspective view of one embodiment of the modular trocar system of the present disclosure.
Figure 2:
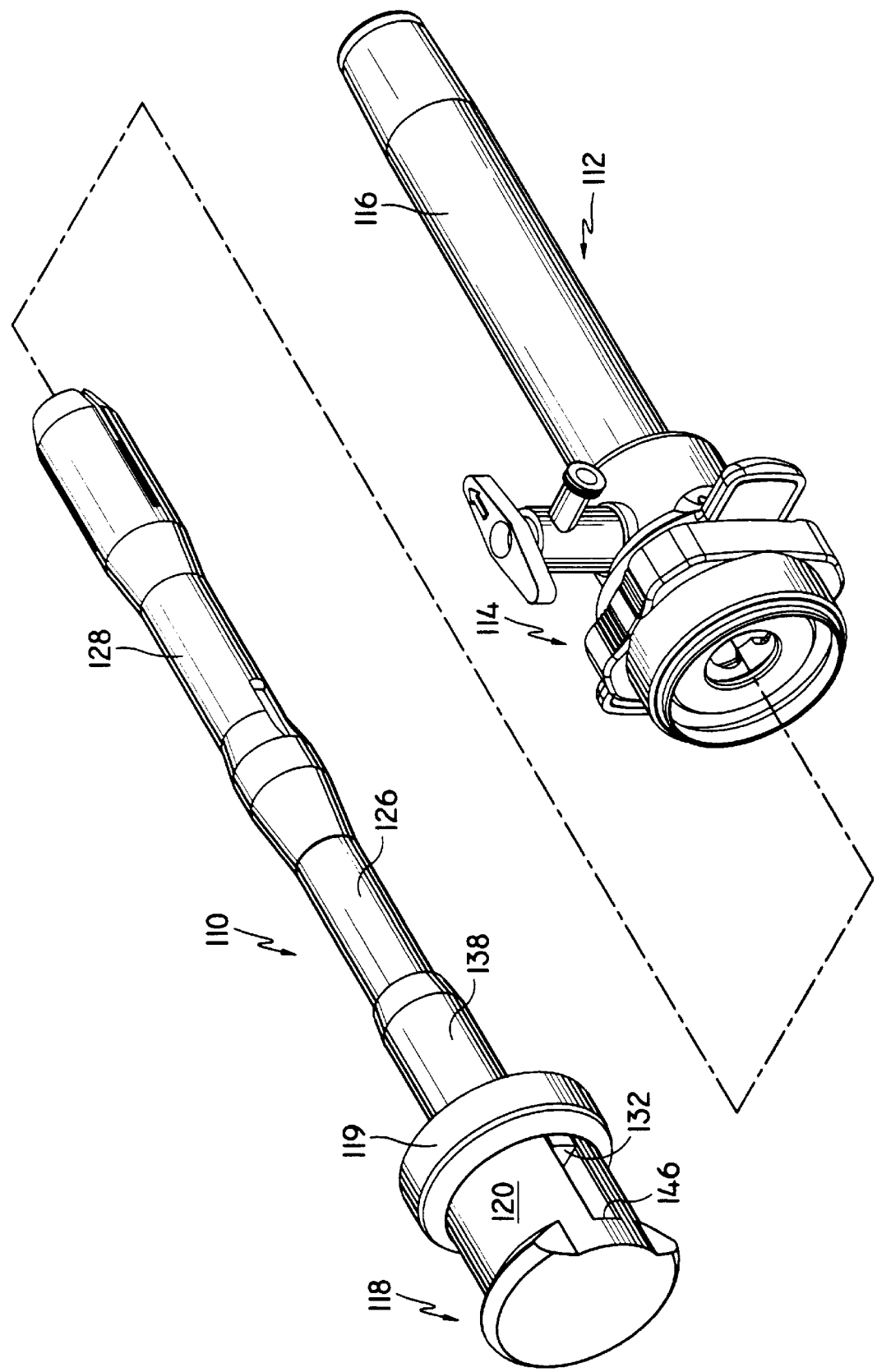
FIG. 2 is a perspective view with parts separated of the modular trocar system of embodiment of FIG. 1.
Figure 2A:
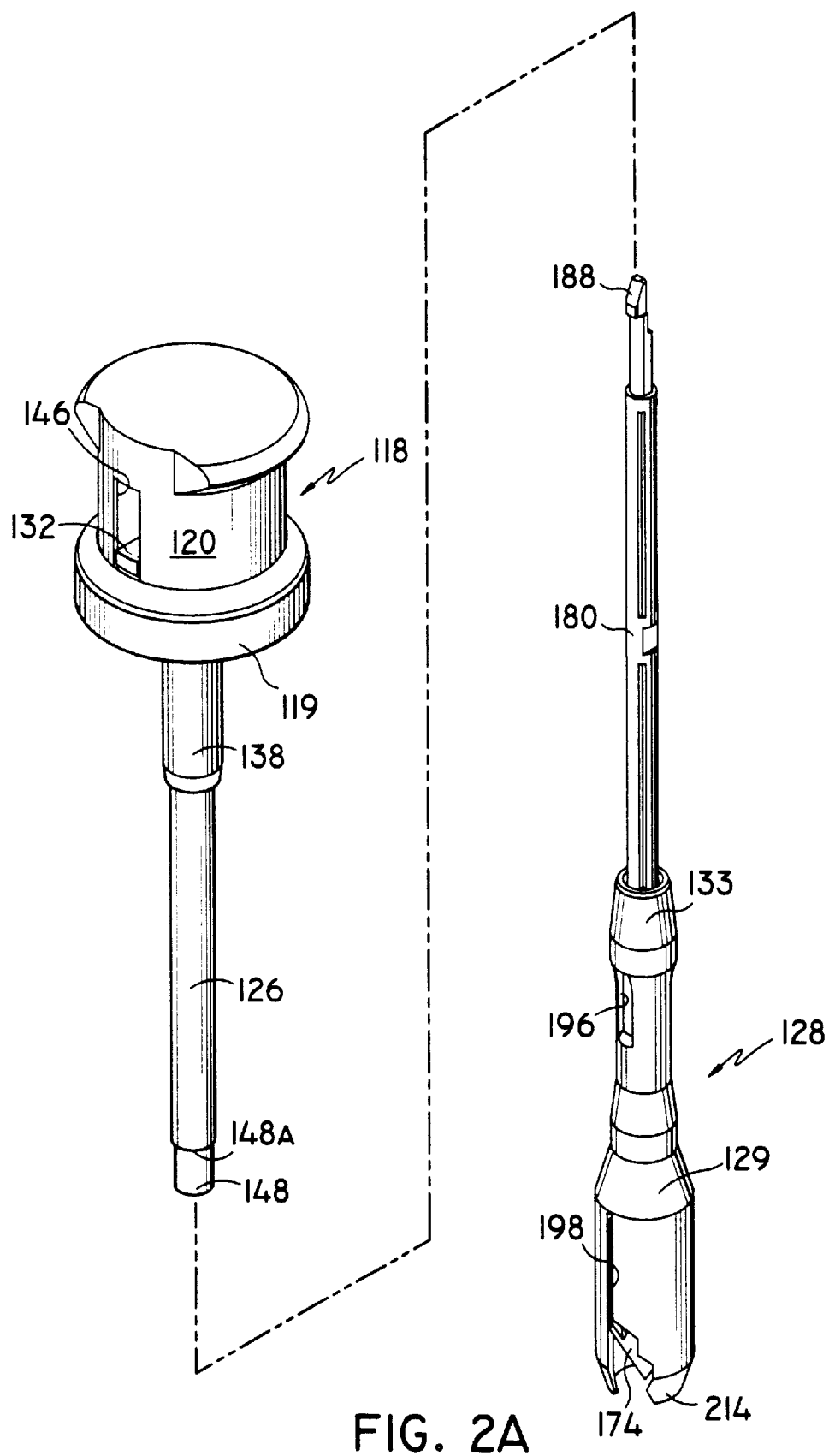
FIG. 2A is an exploded perspective view, partially in section, showing first and second subassemblies of the modular trocar system.

Referring initially to FIGS. 1 and 2, one embodiment of a modular trocar system in accordance with the present disclosure is designated by reference numeral 100 throughout the several views. Modular trocar system 100 is particularly adapted for use in minimally invasive surgical procedures such as endoscopic or laparoscopic procedures. Generally, modular trocar system 100, when assembled into its two principal subassemblies, includes an obturator assembly 110 and a cannula assembly 112. The cannula assembly includes a valve assembly 114 and a cannula 116, as described in detail further herein.

Except where noted otherwise, the materials utilized in the components of the presently disclosed modular trocar system generally include materials such as either ABS or polycarbonate for housing sections and related components and stainless steel for components that are required to cut tissue. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Referring now to FIG. 3, obturator assembly 110 includes an obturator housing 118 formed from housing base 119 and cylindrical housing cover 120. Once the appropriate components are positioned therewithin (as discussed below), housing base 119 may be attached to cylindrical housing cover 120 by engaging mating surfaces, for example by resilient latches 122 formed on cover 120 interlocking with correspondingly shaped engaging surfaces 123 formed in the housing base 119. To uniformly connect base 119 and cover 120, preferably at least three corresponding latches 122 and engaging surfaces 123 are provided and are spaced evenly around the circumference of cover 120 and housing base 119, respectively. Base 119 and cover 120 are preferably molded from an ABS material and are preferably configured and dimensioned to functionally cooperate with various sizes of cannulas, e.g., 5–15 mm. Thus, obturator housing 118 is adapted to be a modular component for use with a wide range of trocar assemblies.

When fully assembled, obturator assembly 110 includes a safety shield that is movable with respect to knife blade 174 and that includes an elongated shield member 126 and a distal shield member 128, both of which are preferably molded from a polycarbonate material. The distal end of elongated shield member 126 is provided with a reduced diameter portion 148 to define a shoulder 148a and to facilitate interaction with distal shield member 128, as discussed below. Elongated shield member 126 also includes proximal end portion 130 having a shield position indicator, such as indicator post 132, extending transversely relative to elongated shield member 126. Preferably post 132 is colored to contrast sharply with the housing components. For example, indicator post 132 may be red if the housing components are white or light colored. Proximal end portion 130 further includes a transverse bearing surface 134.

Elongated shield member 126 is disposed within a longitudinal throughbore 136 formed through cylindrical extended portion 138 of housing base 119 with bearing surface 134 abutting housing base 119 on a proximal face thereof. Cylindrical extended portion 138 may be molded as part of housing base 119 or, preferably, molded separately and mounted to housing base 119, e.g., by sonic welding. Cylindrical extended portion 138 provides transverse support to the shield and obturator components that pass therethrough and preferably includes an inward taper at its distal end to facilitate passage through valve/seal assemblies. Abutment between transverse bearing surface 134 and housing base 119 limits distal movement of shield member 126 relative thereto. Transverse bearing surface 134 also interacts with a guide rail 121 molded within cover 120 (see FIG. 6) to assist in the angular orientation of shield member 126 relative to housing 118.

As best seen in FIGS. 6, 8 and 9, housing cover 120 preferably includes a distally directed, hollow cylindrical post 144 molded to the proximal face thereof. Although hollow post 144 serves several functions, initially it is noted that coil spring 140, which biases shield member 126 toward a distal-most position through abutment with an annular flange 135 on shield member 126 (see FIG. 6), is positioned around hollow cylindrical post 144. Thus, hollow post 144 assists in alignment of coil spring 140, e.g., to prevent kinking thereof. The diameter of coil spring 140 may be reduced in the region adjacent annular flange 135 so as to fit snugly within proximal extension 142 of shield member 126.

Housing cover 120 is further provided with an open ended slot 146 to slidably receive position indicator post 132. Housing cover 120 may further be provided with indicia (not shown) positioned adjacent open ended slot 146 to provide additional visual indication to the user of the relative positioning of the shield, as is known in the art.

As noted above, the shield member 126 (and therefore the entire shield mechanism) is biased in a distal-most position by coil spring 140. A latching mechanism is provided to prevent proximal movement of the shield mechanism until such a time as obturator assembly 110 is inserted in a cannula assembly, e.g., cannula assembly 112, and the surgeon is prepared to begin trocar entry. The preferred latching mechanism is substantially as described in commonly assigned U.S. Pat. No. 4,902,280 to Lander, the entire contents of which are incorporated herein by reference.

Briefly, the latching mechanism includes a latch member 150 having two leg portions 152 and 154. Latch member 150 is securely mounted to housing base 119 through interaction between leg portion 152 and bracket 156, and further interaction between the U-shaped portion of latch member 150 and molded receiving portion 158. Leg portion 154 is resiliently flexible toward and away from leg portion 152. In a relaxed condition, leg portion 154 is spaced away from leg portion 152 such that extended portion 160 contacts abutment surface 134a (see FIG. 6) of elongated shield member 126 to inhibit proximal movement thereof. Leg portion 154 is further provided with extended resilient finger 162 which abuts a ridge 164 formed in release member 166 which is movably mounted relative to housing base 119.

Release member 166 is distally biased by a coil spring 168 which is maintained in axial alignment with the proximal end of release member 166 by post 170. The proximal end of coil spring 168 bears against the inner surface of housing cover 120. The distal biasing of release member 166 causes pin 172, which extends distally from the distal face of release member 166, to project through an opening formed in the housing base 119. Compression of obturator assembly 110 relative to cannula assembly 112 causes release member 166 to be urged in a proximal direction. This proximal motion of release member 166 urges extended finger 162 toward a more vertical orientation, thereby increasing its effective height and flexing leg portion 154 toward leg 152 and out of axial alignment with abutment surface 134a of elongated shield member 126, thereby releasing the latching mechanism. As described, in the Lander '280 patent, the latching mechanism automatically resets upon return of the shield mechanism to its distal-most position.

In a preferred embodiment, the components heretofore described, namely housing base 119, housing cover 120, the latching mechanism components, coil spring 140, cylindrical extended portion 138 and elongated shield member 126 constitute a first modular subassembly that may be advantageously manufactured in large quantities and inventoried for use across a wide range of trocar assembly sizes. As noted hereinbelow, other modular subassemblies may be manufactured to different size specifications, e.g., 5 mm, 10 mm, 15 mm, but all would be functionally operable with the first modular subassembly disclosed herein.

Referring again to FIGS. 3 and 4, assembly of a second modular subassembly including knife blade 174 will now be addressed in detail. Knife blade 174 is preferably fabricated from stainless steel by a suitable process, e.g., by metal injection molding. A method for making metal injection molded medical instruments is disclosed in commonly assigned U.S. Pat. No. 5,308,576 to Green et al., the contents of which are hereby incorporated by reference. Knife blade 174 preferably has a circular base portion 176 which may be hollowed out as shown in FIG. 4 or may be formed of a solid material as in knife blade 174' shown in FIG. 4A, such as by machining from a solid block of stainless steel. The hollowed out embodiment of the knife blade reduces the weight of the knife without affecting the performance characteristics thereof.

A proximally extending elongated portion 178 is provided to facilitate mounting of knife blade 174 to knife rod 180. Elongated portion 178 is provided with a spindle 182 formed at a proximal end for interfitting in a notch 184 formed near the distal end of knife rod 180. Spindle 182 is mounted to knife rod 180 by inserting spindle 182 through an opening 184 formed in the outer surface of knife rod 180 and assuming an abutting relation with flange 186 formed in knife rod 180 distal thereof. Of note, the features and geometries of knife rod 180 are such that this component may be manufactured in large quantities to be utilized in trocar assemblies, regardless of the diameter of such trocar assembly. Only when the knife rod is joined to a knife blade 174 and a distal shield member 128 is its use limited to a specific trocar assembly diameter.

Referring now to FIGS. 5–9, once knife blade 174 is mounted to knife rod 180, distal shield member 128 functions to maintain knife blade 174 in axial alignment with knife rod 180. More particularly, as shown in FIGS. 6 and 7, the close proximity of the inner wall of distal shield member 128 to the point of connection between spindle 182 and knife rod 180 prevents separation thereof. Spindle 182 and opening 184 are each configured and dimensioned to permit free rotational movement of knife blade 174 with respect to knife rod 180, while ensuring and maintaining a fixed relative longitudinal relationship therebetween.

During assembly, knife blade 174 is inserted in knife rod 180, as described above, and the joined components are then passed through distal shield member 128 (from the distal end of distal shield member 128) at least until stops 190 formed on the outer surface of knife rod 180 pass under and proximally of arcuate, inwardly tapered shelf portion 192 formed in the inner surface of distal shield member 128 in neck region 194 thereof. Stops 190 preferably include camming ramps 191 (see FIG. 7) and the camming interaction between camming ramps 191 and shelf portion 192 causes stops 190 to deflect inwardly, as facilitated by slot 193 formed through knife rod 180, to allow stops 190 to pass proximal of shelf portion 192. Once proximal of shelf portion 192, stops 190 flex back to their original position, thereby preventing distal shield member from sliding distally off of knife rod 180. As thus assembled, a second modular subassembly is provided that may be advantageously manufactured in large quantities and inventoried for use insofar as trocar assemblies requiring the specific knife/shield diameter are required.

Referring to FIGS. 7 and 7A, longitudinal openings 196 are advantageously provided in opposite sides of distal shield member 128 to permit inward deflection of stops 190 and separation of distal shield member from knife blade 174, if so desired. In this way, reclamation of individual components is possible for any reason, e.g., if it is determined by manufacturing personnel that knife rod 180 is best utilized with a different size knife blade/distal shield member combination. Shelf portion 192 is preferably formed at or near the distal end of longitudinal openings 196 to facilitate access to stops 190. A disassembling forceps-type tool (not pictured) may be provided to facilitate separation of the components. Thus, the jaws of the disassembly tool may be maneuvered through opposing longitudinal openings 196 to compress knife rod 180 such that stops 190 are compressed to a smaller dimension than shelf 192 to permit stops 190 to pass distally below shelf 192.

Relative distal movement of knife blade 174 and knife rod 180 relative to distal shield member 128 are thus limited by abutment between stops 190 and shelf 192. Relative distal movement of distal shield member 128 relative to knife blade 174 and knife rod 180 is also limited. In particular, distal shield member 128 includes a radially, inwardly directed abutment flange 131 adjacent tapered portion 129 that is adapted to abut a proximal face 177 of knife blade 174 when distal shield member 128 is in its distal-most position relative to knife blade 174 and knife rod 180. When the distal shield member 128 is in its distal-most position fins 200 on knife blade 174 are closely adjacent, if not touching, the proximal ends of longitudinal slots 198 formed in distal shield member 128, as discussed in more detail below.

The geometries of and cooperation between knife blade 174 and distal shield member 128 facilitate ease of insertion of modular trocar system 100 through a patient's body wall while maintaining surgeon control and, by reason of spring biased distal shield member 128, providing an enhanced margin of safety to internal organs. Referring to FIG. 4 in conjunction with FIGS. 10 and 11, fins 200 define extended cutting surfaces 210 which extend beyond the circumference of circular base 176 and within slots 198 formed in distal shield member 128. Knife tip portion 212 defines a pyramidal shape having a planar surface 211 between each pair of adjacent cutting edges 210. Knife tip portion 212 may initially be generally formed by metal injection molding and the cutting edges 210 finely sharpened, for example, by machining and/or polishing of the surfaces. Extended cutting surfaces 210 preferably extend radially outwardly to the outer diameter of the cylindrical portion of distal shield member 128, thereby achieving an incision which approximates the diameter of the distal shield member 128. By incising to the diameter of distal shield member 128, the force required for inserting modular trocar system 100 through tissue, such as the patient's abdominal wall, is reduced.

Referring temporarily back to FIG. 6, a further feature of the modular trocar system which facilitates ease of insertion into the patient is that the included angle formed between extended cutting surfaces 210 and the central longitudinal axis of modular trocar system 100 (as represented by section line 8—8 in FIG. 6) is preferably greater than the included angle formed between the beveled distal end 214 formed on distal shield member 128. The included angle formed between extended cutting surfaces 210 and the central longitudinal axis of modular trocar system 100 is represented by the angle "alpha" as measured between the horizontal surface of fin 200, which is preferably parallel to the central longitudinal axis of modular trocar system 100, and the phantom extension of extended cutting surface 210. The included angle formed between beveled distal end 214 and the central longitudinal axis of modular trocar system 100 is represented by the angle labeled "beta", as measured between the horizontal surface of distal shield member 128, which is parallel to the central longitudinal axis of modular trocar system 100 and the phantom extension line of beveled distal end 214. The greater angle alpha causes an initial displacement of tissue which is advantageously greater than that required for any portion of modular trocar system 100 which is proximal of the knife blade 174.

A further feature of the knife blade 174 and the distal shield member 128 is the manner in which beveled distal ends 214 of distal shield member 128 assume a substantially recessed position relative to fins 210 when moved proximally during trocar entry. More particularly, beveled distal ends 214 define substantially straight edges 215. In addition, the region between circular base 176 and respective fins 210 of knife blade 174 define recesses 213 within which edges 215 are adapted to ride when distal blade member 128 moves proximally relative to knife blade 174. Thus, as trocar system 100 is introduced through tissue, the resistance between distal shield member 128 and tissue is minimized by the nesting of beveled distal ends 214 within recesses 213. Preferably, the thickness of beveled distal ends 214 and the angles of edges 215 relative to the angles of fins 210 are such that the nesting or recessing of beveled distal ends 214 is maximized and penetration force minimized.

As best illustrated in FIGS. 8 and 9, to facilitate ease of assembly and modularity, knife rod 180 is provided with a latch portion 188 at a proximal end. Latch portion 188 is in the shape of a ramp so that upon insertion of knife rod 180 into housing cover 120, latch portion 188 is initially cammed away from an opening 189 formed in post 144. Upon further proximal movement of knife rod 180, latch portion 188 passes through opening 189 in post 144 of housing cover 120 and deflects to its initial position, thereby locking knife rod 180 with respect to housing cover 120 to prevent relative longitudinal or rotational movement between the two components. In addition, distal shield member 128 includes a proximal region 133 (of increased inner diameter relative to reduced diameter portion 148 on elongated shield member 126) defining an abutment face 135. When assembled, abutment face 135 contacts shoulder 148a on elongated shield member 126 so as to create an interactive shield mechanism extending substantially the effective length of obturator assembly 110.

Consistent with the modularity of trocar assembly 100 described herein, an elongated probe type instrument (not shown) may be provided for easy insertion through opening 146 (FIG. 2) to urge latch portion 188 out of opening 146. In this way, reclamation of components may be easily accomplished if it determines, e.g., that a different knife blade/distal shield member subassembly should be assembled with a given obturator housing subassembly.

The rotational relationship of knife blade 174 with respect to knife rod 180 and the fixed relationship of knife rod 180 with respect to housing cover 120 facilitates the relative rotational movement of knife blade 174 with respect to housing cover 120. Similarly, the rotational relationship of proximal region 133 of distal shield member 128 and reduced diameter portion 148 of elongated shield member 126 facilitates the relative rotational movement of distal shield member 128 relative to elongated shield member 126 and thus housing cover 120. Accordingly, twisting of housing cover 120 by the user upon insertion of modular trocar system 100 into the patient does not affect the positioning of knife blade 174 relative to the patient's body tissue once knife blade 174 comes into contact with the tissue.

Figure 12:
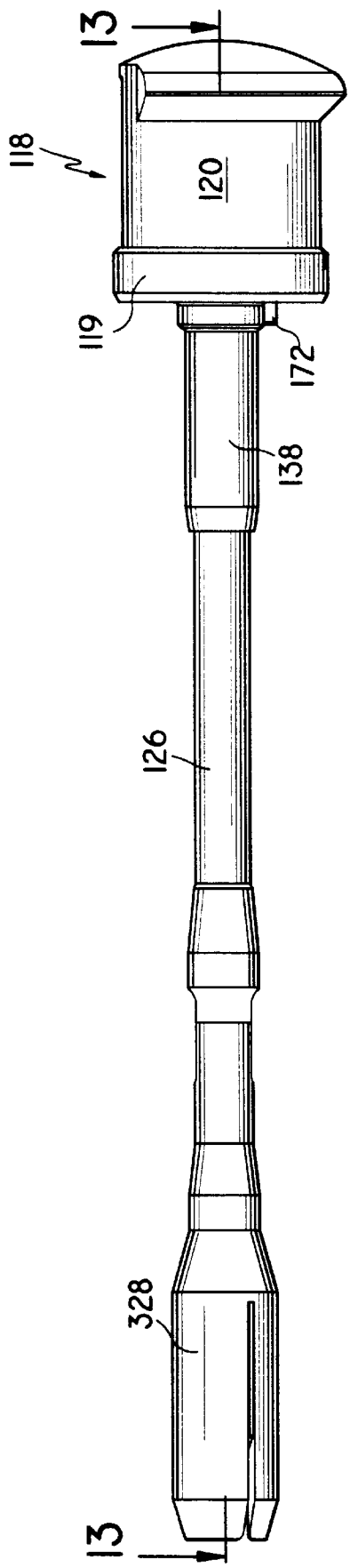
FIG. 12 is a plan view of an alternate embodiment of the modular trocar assembly which shows the same sized proximally disposed components fitted with a larger sized knife and knife shield.
Figure 13:
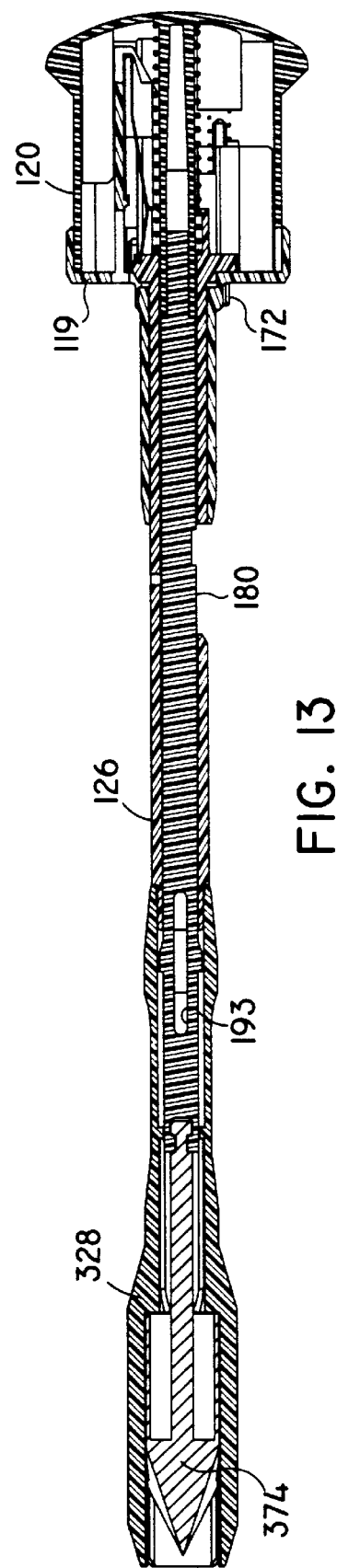
FIG. 13 is a cross-section view taken along section line 13—13 of FIG. 12.
Figure 16:
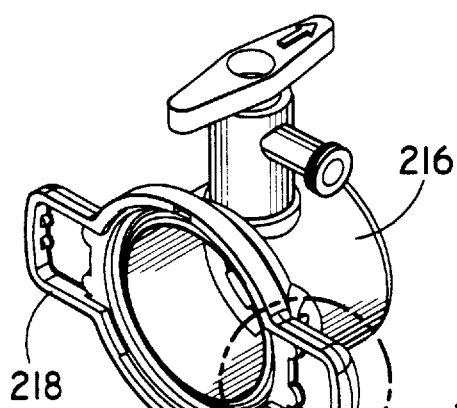
FIG. 16 is a perspective view of the cannula assembly valve housing.

FIGS. 12 and 13 are useful in illustrating the benefits associated with the modular aspects of the obturator assembly of modular trocar system 100. As shown, each of the components of obturator assembly 110 are the same except a larger sized knife blade 374 and distal shield member 328 have been attached to knife rod 180 and elongated tubular member 180 (as compared to the trocar system of FIGS. 6 and 8), respectively. This interchangeability of different sized knives and distal shield members with standard sized components located proximally thereof obviates the need to manufacture and inventory both the components and whole units of non-modular, conventional trocar systems. In particular, the more complex and, therefore, more expensive size-specific elements located in the obturator housing need not be manufactured and inventoried. The manufacturer or distributor need only assemble the appropriate sized knife and distal shield member with the otherwise standard sized control components as demand dictates.

Referring now to FIGS. 14–17, cannula assembly 112 of modular trocar system 100 will now be described in greater detail. Cannula assembly 112 includes a molded cylindrical base portion 216 having transversely extending grip portions 218 formed to extend form an annular flange formed at the proximal end of cylindrical base 216. A series of slots 222 are formed along the underside or distal side of grips 218.

Figure 17:
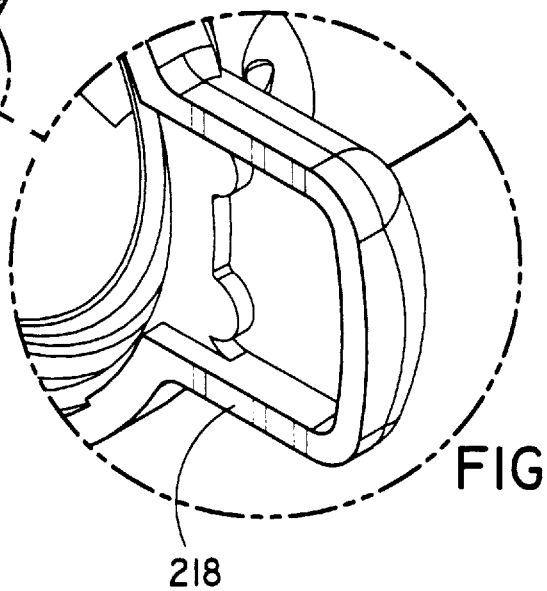
FIG. 17 is an enlarged view of the indicated area of detail shown in FIG. 16.

Slots 222 are particularly advantageous in two respects. First, in assembling cannula assembly 112, there are three basic principle components: cylindrical base portion 216 having outwardly directing finger grips 218, a duck bill valve element 224 having a flange 226 which is configured and dimensioned to rest on annular flange 220 of cylindrical base portion 215 and a cannula housing cover portion such as proximal housing element 228 which is configured and dimensioned to rest on duck bill flange 226 and within the outwardly directed finger grips 218. It has been found that by coring out the underside of outwardly extending finger grips 218 with parallel slots 222, molding sinks which had been previously forming on the proximal side of outwardly extending fingers 218 of cylindrical base portion 218 were significantly reduced, thereby providing a much more reliable flat surface, as best shown in FIG. 17, against which duck bill flange 226 may rest and against which the upper or proximal housing element 228 may be welded.

This greater cooperation between the two cannula housing elements reduces the force which must be applied as between the two housing elements during the welding process, thereby reducing the likelihood that the duck bill valve 224 will be torqued. Torquing of the duck bill valve 224 can potentially reduce the sealing function of the element in the absence of a surgical instrument inserted therethrough.

The second respect in which slots 222 are advantageous is that on the underside of the cylindrical base portion 216 is normally the place where the user grips the cannula the cylindrical base portion 216. Accordingly, the slots provide an improved gripping surface to the user.

A further feature of cannula assembly 112 is the provision of a detachable cannula 116 which readily connects and disconnects from cylindrical base portion 216. Cannula 116 is preferably molded with a substantially constant inner and outer diameter. However, cannula 116 preferably includes a slightly larger inner diameter at its proximal end, e.g., of 2–3 cms length, to facilitate introduction of instrumentation, and a tapered outer diameter at its distal-most portion, e.g. over the distal-most 2–3 cms of length, the tapered outer diameter being largest at a proximal end thereof and smallest at a distal end thereof. In this way, molding is facilitated while penetration force is minimized by reducing the outer diameter of cannula 116 in the region where tissue first makes contact and by providing a gradual taper to the outside diameter to assist in dilation of tissue as it passes proximally along the outer wall of cannula 116.

An elastomeric O-ring 230 is interposed between cylindrical base portion 216 and cannula 116 to maintain a fluid-type seal between cannula 116 and cylindrical base portion 216. Cannula 116 is formed of a predetermined diameter so as to form a longitudinal throughbore 232 in communication with a passageway formed through cylindrical base portion 216 and proximal housing element 228. Cannula 116 is further provided with an annular flange 234 which is particularly sized to be received in the distal end of cylindrical base portion 216. Flange 234 is preferably a standard size such that cannulas having different sized diameter passageways formed therethrough may be formed with a flange that has the same configuration and dimension as flange 234. In this manner, cannulas of varying sized and dimensions may be interchangeably attached to a given cylindrical base portion such cylindrical base portion 216.

To facilitate the interconnectability of cannula 116 and cylindrical base portion 216, a quick connect mechanism is provided which, for example, may be by a series of engageable mating members 236 formed on cannula 116 proximal of flange 234 which interconnect cannula 116 with cylindrical base portion 216 by way of a series of mating indented surfaces 238 formed along the inner wall of cylindrical base portion 216. The two elements are brought into engagement with each other by inserting the proximal end of cannula 116 into the distal end of cylindrical base portion 216 and rotating cannula 116 clockwise until mating members 236 engage and lock into mating surfaces 238. The two elements may be disengaged by applying a proximally directed force to the cannula toward cylindrical base portion 216 and rotating cannula 116 counterclockwise. This feature is particularly advantageous during manufacture and assembly of cannula assembly 112 in that it facilitates inventory management and manufacturing efficiencies due to the cylindrical base portion 216 now being a single component which is able to be utilized across multiple cannula diameter products, the only difference being the cannula which is ultimately secured to the cylindrical base portions at the final stage of manufacture.

Also provided on cannula assembly 112 is a seal assembly 240 which generally includes a housing 242, a seal member 244 and a plurality of spreading members (not shown) which serve to spread an orifice 246 of the seal member to accommodate instruments of different diameters therethrough while maintaining a fluid-tight seal. A similar seal assembly is commercially available with the VERSAPORT™ trocar system manufactured by United States Surgical Corporation, Norwalk, Conn.

Figure 18:
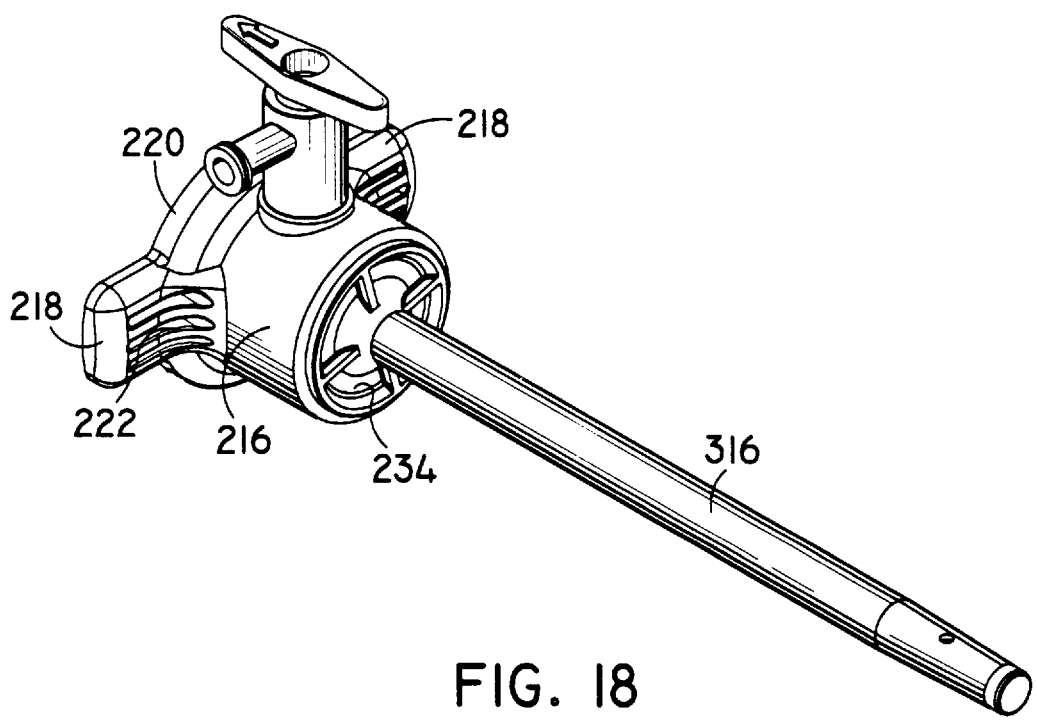
FIG. 18 is a further embodiment of the cannula assembly of the modular trocar system of the present disclosure.

Referring to FIG. 18, the interchangeability of different sized cannulas with the same sized housing is illustrated by smaller cannula 316 shown attached to cannula 216. This feature greatly simplifies the problem of manufacturing and keeping an inventory of numerous different diameter cannula assemblies.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of assembling an obturator assembly for use in a trocar system comprising the steps of:

connecting a shield member of a first predetermined configuration and dimension to a first housing section;

attaching a knife blade assembly of a second predetermined configuration and dimension to the first housing section with a single motion wherein the attachment permits rotation of the knife blade relative to the first housing section; and attaching the first housing section to a second housing section with a quick connect mechanism which includes first and second mating portions such that the first and second housing sections are movable from a spaced apart position to a connected position in a single motion.

2. A method of assembling a trocar system, comprising the steps of:

connecting a first housing which includes a valve assembly disposed in a passageway formed between an open proximal end and an open distal end, with a cannula which defines a passageway of a predetermined size therethrough;

connecting a shield member of a first predetermined configuration and dimension to a second housing section;

attaching a knife blade assembly of a second predetermined configuration and dimension to the second housing section with a single motion wherein the attachment permits rotation of the knife blade relative to the second housing section;

attaching the second housing section to a third housing section with a quick connect mechanism which includes first and second mating portions such that the second and third housing sections are movable from a spaced apart position to a connected position in a single motion; and inserting the shield member and knife blade assembly into the open proximal end of the first housing such that at least a portion of the shield member extends through the cannula.

3. The method according to claim 2, wherein the step of connecting the first housing to the cannula includes aligning a third mating portion, formed on the first housing, with a fourth mating portion, formed on the cannula, and moving the first housing and the cannula from a spaced apart relative orientation to an attached orientation, wherein the third and fourth mating portions are engaged.

4. The method according to claim 3, which further comprises the step of forming a fluid-tight seal between the first housing and the cannula.

* * * * *